(12) United States Patent
Izu et al.

(10) Patent No.: US 11,103,415 B2
(45) Date of Patent: Aug. 31, 2021

(54) WALKING TRAINING SYSTEM AND METHOD OF CONTROLLING THE SAME

(71) Applicant: TOYOTA JIDOSHA KABUSHIKI KAISHA, Toyota (JP)

(72) Inventors: Hiroki Izu, Nagoya (JP); Yu Sasaki, Toyota (JP); Kazuya Yamamoto, Miyoshi (JP); Uori Koike, Toyota (JP); Masatomo Tanaka, Toyota (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 413 days.

(21) Appl. No.: 16/132,881

(22) Filed: Sep. 17, 2018

(65) Prior Publication Data

US 2019/0105218 A1  Apr. 11, 2019

(30) Foreign Application Priority Data

Oct. 5, 2017 (JP) .............................. JP2017-195006

(51) Int. Cl.
*A61H 3/00* (2006.01)
*A61H 1/02* (2006.01)
(Continued)

(52) U.S. Cl.
CPC ............. *A61H 3/008* (2013.01); *A61H 1/024* (2013.01); *A61H 1/0255* (2013.01); *A61H 3/00* (2013.01);
(Continued)

(58) Field of Classification Search
CPC ........ A61H 1/024; A61H 1/0255; A61H 3/00; A61H 3/008; A61H 2201/1215;
(Continued)

(56) References Cited

U.S. PATENT DOCUMENTS 5,800,314 A * 9/1998 Sakakibara ............ A63B 22/02
  482/1
2006/0229167 A1* 10/2006 Kram ............... A63B 21/00181
  482/54

(Continued)

FOREIGN PATENT DOCUMENTS

JP    2000-206862 A    7/2000
JP    2010-240126      10/2010
(Continued)

*Primary Examiner* — Tu A Vo
*Assistant Examiner* — Alexander Morales
(74) *Attorney, Agent, or Firm* — Oblon, McClelland, Maier & Neustadt, L.L.P.

(57) ABSTRACT

A walking training system includes: a treadmill on which a walking trainee walks; a walking assistance apparatus that is mounted on a leg part of the walking trainee and assists walking of the walking trainee; and control means for controlling an operation of the walking assistance apparatus. The control means controls the operation of the walking assistance apparatus so as to cause the walking trainee to approach a reference position when the trainee is spaced apart from the reference position of the treadmill by a predetermined distance or more in a walking front/back direction while the walking trainee is walking on the treadmill, and increases the predetermined distance when at least one of a walking training amount of the walking trainee, a walking training level of the walking trainee set in the walking training system, and the speed of the treadmill is larger/higher/greater than a predetermined amount, level, and speed.

6 Claims, 6 Drawing Sheets

(51) Int. Cl.
  *G16H 40/63* (2018.01)
  *A63B 24/00* (2006.01)
  *B66D 1/00* (2006.01)
  *A63B 22/02* (2006.01)
  *B25J 9/00* (2006.01)
  *G09B 19/00* (2006.01)

(52) U.S. Cl.
  CPC ......... *A63B 24/0087* (2013.01); *B25J 9/0006* (2013.01); *G16H 40/63* (2018.01); *A61H 2201/1215* (2013.01); *A61H 2201/164* (2013.01); *A61H 2201/165* (2013.01); *A61H 2201/1642* (2013.01); *A61H 2201/5061* (2013.01); *A61H 2201/5064* (2013.01); *A61H 2201/5092* (2013.01); *A63B 22/02* (2013.01); *A63B 22/0235* (2013.01); *A63B 2024/0093* (2013.01); *B66D 1/00* (2013.01); *G09B 19/0038* (2013.01)

(58) Field of Classification Search
  CPC ...... A61H 2201/164; A61H 2201/1642; A61H 2201/165; A61H 2201/5061; A61H 2201/5064; A61H 2201/5092; G09B 19/003; G09B 19/0038; B25J 9/0006
  USPC .................................................. 434/255, 247
  See application file for complete search history.

(56) References Cited

U.S. PATENT DOCUMENTS

| | | | |
|---|---|---|---|
| 2007/0255186 A1* | 11/2007 | Grill | A63B 22/02 600/595 |
| 2014/0058299 A1* | 2/2014 | Sankai | A61H 3/00 601/35 |
| 2016/0106618 A1 | 4/2016 | Matsumoto et al. | |
| 2016/0253890 A1* | 9/2016 | Rabinowitz | A61B 5/1113 340/539.13 |
| 2016/0296800 A1* | 10/2016 | Devor | A63B 24/0062 |
| 2017/0027803 A1* | 2/2017 | Agrawal | A61B 5/224 |
| 2018/0033321 A1* | 2/2018 | Clarke | B29D 23/00 |

FOREIGN PATENT DOCUMENTS

| | | |
|---|---|---|
| JP | 2012-95793 | 5/2012 |
| JP | 2016-93411 A | 5/2016 |
| JP | 2018-130234 | 8/2018 |
| WO | WO 2015/049910 A1 | 4/2015 |

* cited by examiner

WALKING TRAINING SYSTEM AND METHOD OF CONTROLLING THE SAME

CROSS REFERENCE TO RELATED APPLICATIONS

This application is based upon and claims the benefit of priority from Japanese patent application No. 2017-195006, filed on Oct. 5, 2017, the disclosure of which is incorporated herein in its entirety by reference.

BACKGROUND

The present disclosure relates to a walking training system that performs walking training of a walking trainee and a method of controlling the same.

A walking training system that adjusts the speed of a treadmill in accordance with a motion of a leg attachment that a walking trainee wears has been known (see Japanese Unexamined Patent Application Publication No. 2012-095793). Further, a walking training system that adjusts the speed of a treadmill in accordance with a motion of a foot part of a walking trainee has been known (see Japanese Unexamined Patent Application Publication No. 2010-240126).

SUMMARY

When, for example, the treadmill moves at a constant speed, it is possible that the walking trainee may be greatly behind a reference position of the treadmill. In this case, it is difficult for the walking trainee to continue the training, which causes a decrease in the continuity of the training. In the walking training systems according to related art, it is possible to adjust the speed of the treadmill and continue the training. This may cause, however, another problem that a training effect is reduced, one reason for which is that the walking trainee excessively depends on the speed adjustment of the treadmill. Furthermore, as walking trainees have walking levels different from one another, this makes the aforementioned problems even more complicated. It has thus been demanded to achieve both continuity of the walking training and suppression of the reduction in the training effect in accordance with the walking level of each walking trainee.

The present disclosure has been made in order to solve the aforementioned problems, and aims to provide a walking training system and a method of controlling the same capable of achieving both continuity of the walking training and suppression of the reduction in the training effect in accordance with the walking level of each walking trainee.

One aspect of the present disclosure to accomplish the aforementioned object is a walking training system including: a treadmill on which a walking trainee walks; a walking assistance apparatus that is mounted on a leg part of the walking trainee and assists walking of the walking trainee; and control means for controlling an operation of the walking assistance apparatus, in which the control means controls the operation of the walking assistance apparatus in such a way as to cause the walking trainee to approach the reference position when the walking trainee is spaced apart from the reference position of the treadmill by a predetermined distance or more in a walking front/back direction while the walking trainee is walking on the treadmill, and the control means increases the predetermined distance when at least one of a walking training amount of the walking trainee, a walking training level of the walking trainee set in the walking training system, and the speed of the treadmill is larger/higher/greater than a predetermined amount, level, and speed.

In the aforementioned aspect, the control means may perform control to decrease an assisting power of the walking assistance apparatus in such a way as to cause the walking trainee to approach the reference position when the walking trainee is spaced apart from the reference position of the treadmill by a predetermined distance or more in a walking forward direction, and the control means may perform control to increase the assisting power of the walking assistance apparatus in such a way as to cause the walking trainee to approach the reference position when the walking trainee is spaced apart from the reference position of the treadmill by a predetermined distance or more in a walking backward direction.

In the aforementioned aspect, when the walking trainee is spaced apart from the reference position of the treadmill by a predetermined distance or more in a walking front/back direction, the control means may perform control to further increase or decrease the assisting power of the walking assistance apparatus in such a way as to cause the walking trainee to approach the reference position as the distance to the walking trainee from the reference position of the treadmill becomes greater in a walking front/back direction.

In the aforementioned aspect, the control means may control the operation of the walking assistance apparatus in such a way as to cause the walking trainee to approach the reference position when the walking trainee is spaced apart from the reference position of the treadmill by a first predetermined distance or more in a walking forward direction or when the walking trainee is spaced apart from the reference position of the treadmill by a second predetermined distance or more in a walking backward direction, and the first predetermined distance may be set to be greater than the second predetermined distance.

In the aforementioned aspect, the control means may control, when the walking trainee is spaced apart from the reference position of the treadmill by a predetermined distance or more in a walking front/back direction, an operation of the walking assistance apparatus and at least one of the inclination and the speed of the treadmill and a pulling force of a pulling apparatus that pulls the walking trainee upward via a wire in such a way as to cause the walking trainee to approach the reference position.

One aspect of the present disclosure to accomplish the aforementioned object may be a method of controlling a walking training system including: a treadmill on which a walking trainee walks; a walking assistance apparatus that is mounted on a leg part of the walking trainee and assists walking of the walking trainee; and control means for controlling an operation of the walking assistance apparatus, in which the control means controls the operation of the walking assistance apparatus in such a way as to cause the walking trainee to approach a reference position when the walking trainee is spaced apart from the reference position of the treadmill by a predetermined distance or more in a walking front/back direction while the walking trainee is walking on the treadmill, and the control means increases the predetermined distance when at least one of a walking training amount of the walking trainee, a walking training level of the walking trainee set in the walking training system, and the speed of the treadmill is larger/higher/greater than a predetermined amount, level, and speed.

According to the present disclosure, it is possible to provide a walking training system and a method of controlling the same capable of achieving both continuity of the walking training and suppression of the reduction in the training effect in accordance with the walking level of each walking trainee.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

First Embodiment

Hereinafter, with reference to the drawings, embodiments of the present disclosure will be explained.

Figure 1:
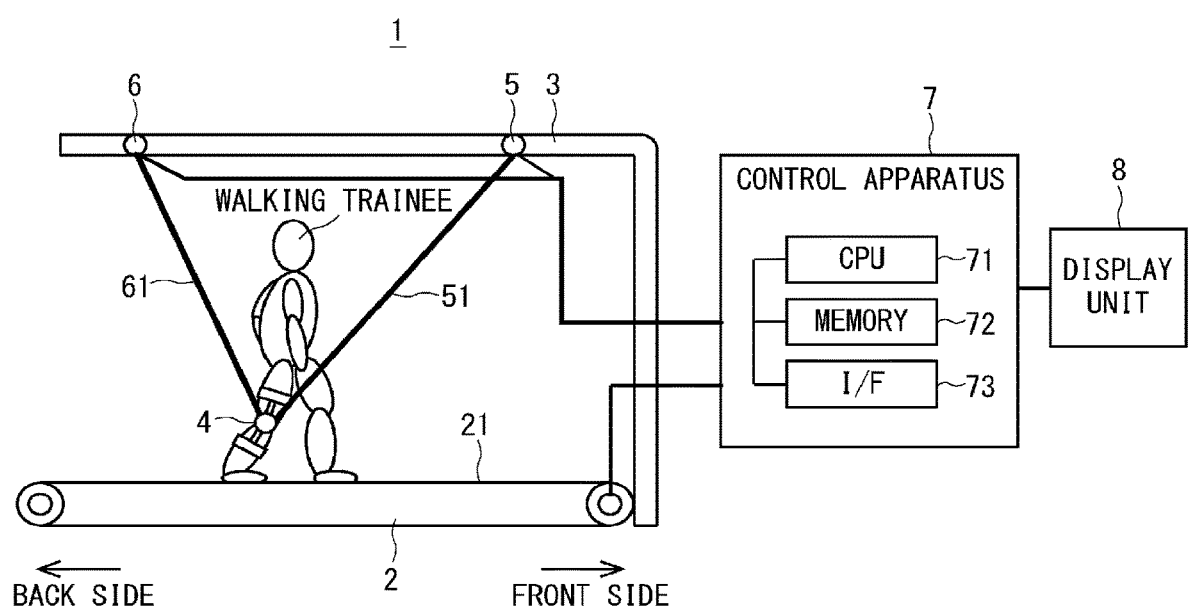
FIG. 1 is a diagram showing a schematic structure of a walking training system according to a first embodiment of the present disclosure.

FIG. 1 is a diagram showing a schematic structure of a walking training system according to a first embodiment of the present disclosure.

A walking training system 1 according to the first embodiment includes a treadmill 2 on which a walking trainee walks, a frame main body 3, a walking assistance apparatus 4 mounted on a leg part of the walking trainee, first and second pulling apparatuses 5 and 6 that pull the walking assistance apparatus 4 upward, and a control apparatus 7 that controls the treadmill 2, the walking assistance apparatus 4, the first pulling apparatus 5, and the second pulling apparatus 6.

The treadmill 2 rotates a ring-like belt 21 by a motor or the like. The user stands on the belt 21 and performs walking in accordance with the movement of the belt 21, thereby performing walking training. The treadmill 2 may include an inclination mechanism that causes the belt 21 to be in an upward inclined state and a downward inclined state in order to adjust the walking load by the walking trainee. The frame main body 3 is installed on the treadmill 2.

Figure 2:
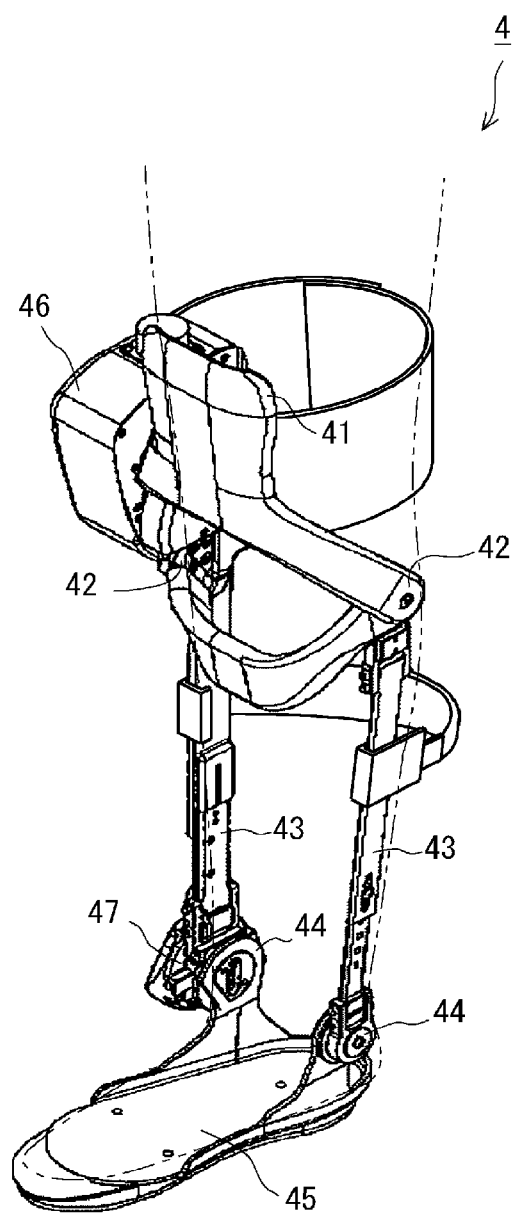
FIG. 2 is a perspective view showing a schematic structure of a walking assistance apparatus.

FIG. 2 is a perspective view showing a schematic structure of the walking assistance apparatus. The walking assistance apparatus 4 is mounted on, for example, the affected leg of the walking trainee, and assists walking of the walking trainee. The walking assistance apparatus 4 includes an upper thigh frame 41, a lower thigh frame 43 coupled to the upper thigh frame 41 via a knee joint part 42, a sole frame 45 coupled to the lower thigh frame 43 via an ankle joint part 44, a motor unit 46 that rotationally drives the knee joint part 42, and an adjustment mechanism 47 that adjusts the movable range of the ankle joint part 44. The motor unit 46 rotationally drives the knee joint part 42 in accordance with the walking by the walking trainee, thereby adding an assisting power to the leg part of the walking trainee. Accordingly, the walking trainee is able to easily walk on the treadmill 2 or the like. The above structure of the walking assistance apparatus 4 is merely one example thereof, and is not limited to the aforementioned one. The walking assistance apparatus 4 may include, for example, a motor unit that rotationally drives the ankle joint part 44.

The first pulling apparatus 5 is provided in a front part of the upper side of the frame main body 3. One end of a wire 51 is connected to the walking assistance apparatus 4 of the leg part of the walking trainee. The first pulling apparatus 5 pulls the walking assistance apparatus 4 upward and frontward via the wire 51.

The second pulling apparatus 6 is provided in a rear part of the upper side of the frame main body 3. One end of a wire 61 is connected to the walking assistance apparatus 4 of the leg part of the walking trainee. The second pulling apparatus 6 pulls the walking assistance apparatus 4 upward and rearward via the wire 61.

The first and second pulling apparatuses 5 and 6 are composed of, for example, mechanisms that wind and rewind the wires 51 and 61, motors that drive these mechanisms and the like. The mechanisms that wind and rewind the wires are each provided with a rotation sensor that detects an amount of rotation when the wires 51 and 61 are wound and rewound.

The first and second pulling apparatuses 5 and 6 pull the walking assistance apparatus 4 mounted on the leg part of the walking trainee upward via the wires 51 and 61, thereby supporting the weight of the walking assistance apparatus 4 and reducing the weight load applied to the leg part of the walking trainee.

The control apparatus 7 is one specific example of control means. The control apparatus 7 controls each of an operation of the walking assistance apparatus 4, pulling forces of the first and second pulling apparatuses 5 and 6, and drive of the treadmill 2. For example, the control apparatus 7 controls the assisting power of the walking assistance apparatus 4. The control apparatus 7 controls the pulling forces of the first and second pulling apparatuses 5 and 6 in such a way as to support, for example, the weight of the walking assistance apparatus 4. The control apparatus 7 controls the speed of the belt 21 of the treadmill 2, the inclination angle of the belt 21 and the like.

The control apparatus 7 is formed of a hardware configuration and mainly includes a microcomputer including, for example, a Central Processing Unit (CPU) 71 that performs operation processing, control processing and the like, a memory 72 that stores an operation program, a control program and the like executed by the CPU 71 and various kinds of data, and an interface unit (I/F) 73 that receives or outputs signals from or to external apparatuses. The CPU 71, the memory 72, and the interface unit 73 are connected to one another via a data bus or the like.

The frame main body 3 is provided with a display unit 8 that displays information such as the training instructions, training menu, walking training information (e.g., walking training amount), the walking training level of the walking trainee, the speed of the treadmill 2, and biometric information). The display unit 8 is formed, for example, as a touch panel. The walking trainee, a trainer and the like are able to input various kinds of information via the display unit 8. The walking trainee inputs, for example, information such as a walking training amount, a walking training level and the like into the control apparatus 7 via the display unit 8.

Incidentally, when, for example, the treadmill moves at a constant speed, it is possible that the walking trainee may be greatly behind a reference position of the treadmill. In this case, it is difficult for the walking trainee to continue the training, which causes a decrease in the continuity of the training. In the walking training systems according to related art, it is possible to adjust the speed of the treadmill and continue the training. This may cause, however, another problem that the training effect is reduced, one reason for which is that the walking trainee excessively depends on the speed adjustment of the treadmill. Furthermore, as walking trainees have walking levels different from one another, this makes the aforementioned problems even more complicated. It has thus been demanded to achieve both continuity of the walking training and suppression of the reduction in the training effect in accordance with the walking level of each walking trainee.

On the other hand, in the walking training system 1 according to the first embodiment, the control apparatus 7 controls the operation of the walking assistance apparatus 4 in such a way as to cause the walking trainee to approach the reference position when the walking trainee is spaced apart from the reference position of the treadmill 2 by a predetermined distance or more in the walking front/back direction while the walking trainee is walking on the treadmill 2. Further, when at least one of a walking training amount of the walking trainee, a walking training level of the walking trainee set in the walking training system 1, and the speed of the treadmill 2 is larger/higher/greater than a predetermined amount, level, and speed, the control apparatus 7 increases the predetermined distance.

As described above, the walking training system 1 according to the first embodiment controls, when the walking trainee is spaced apart from the reference position of the treadmill 2 by the predetermined distance or more in the walking front/back direction, the operation of the walking assistance apparatus 4 in such a way as to cause the walking trainee to approach the reference position. Accordingly, the walking trainee can easily approach the reference position, whereby the continuity of the walking training can be maintained.

Further, when the walking trainee is not spaced apart from the reference position of the treadmill 2 by the predetermined distance or more, the operation of the walking assistance apparatus 4 is not controlled. Accordingly, within the predetermined distance from the reference position, the walking trainee executes walking by himself/herself without depending on the operation adjustment of the walking assistance apparatus 4. Accordingly, the walking training effect can be maintained.

Further, as described above, when at least one of the walking training amount of the walking trainee, the walking training level of the walking trainee set in the walking training system 1, and the speed of the treadmill 2 is larger/higher/greater than a predetermined amount, level and speed, the predetermined distance is increased. Accordingly, when at least one of the walking training amount of the walking trainee, the walking training level, and the speed of the treadmill 2 is large, the predetermined distance is increased, which makes it difficult for the walking trainee to return to the reference position on the treadmill 2. Accordingly, it is possible to achieve both continuity of the walking training and maintenance of the training effect in accordance with the walking level of the walking trainee. That is, it is possible to achieve both continuity of the walking training and suppression of the reduction in the training effect in accordance with the walking level of each walking trainee.

Figure 3:
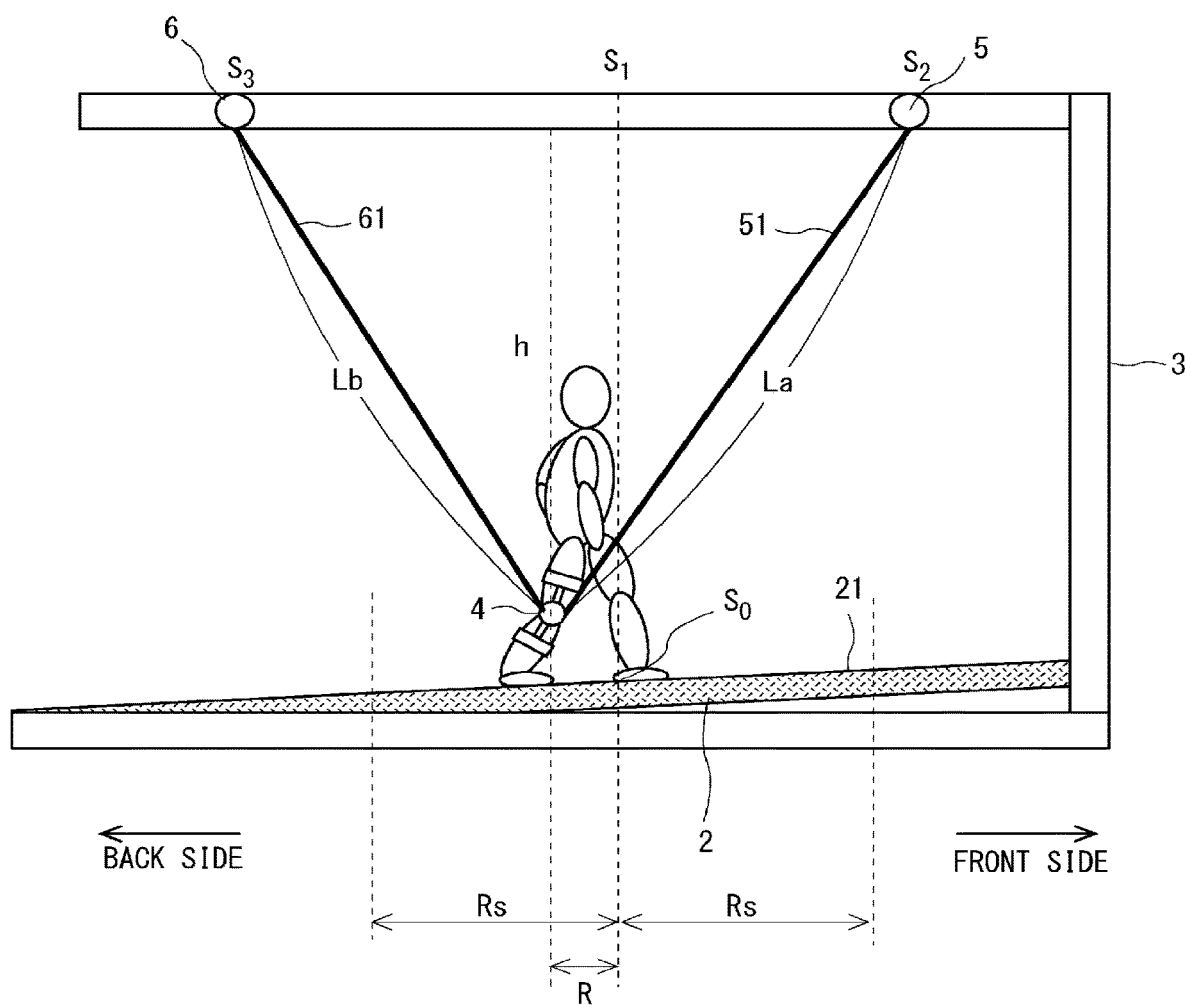
FIG. 3 is a diagram showing a reference position of a treadmill.

FIG. 3 is a diagram showing the reference position of the treadmill.

A reference position $S_0$ of the treadmill 2 is, for example, the position at which the walking trainee performs safe walking on the treadmill 2, and the position substantially at the center of the treadmill 2 in the front/back direction. The reference position $S_0$ of the treadmill 2 is, for example, a point at which the line extended from a central position $S_1$ of the first and second pulling apparatuses 5 and 6 in the vertically downward direction and the treadmill 2 intersect with each other. The reference position $S_0$ of the treadmill 2 is set, for example, in the memory 72 or the like in advance, and can be arbitrarily set by the walking trainee, the trainer and the like.

The control apparatus 7 calculates the amount of winding-up of each of the wire 51 of the first pulling apparatus 5 and the wire 61 of the second pulling apparatus 6 based on an amount of the rotation detected by a rotation amount sensor. The control apparatus 7 calculates each of a length La of the wire 51 from a position $S_2$ of the first pulling apparatus 5 to the position of the walking assistance apparatus 4 and a length Lb of the wire 61 from a position $S_3$ of the second pulling apparatus 6 to the position of the walking assistance apparatus 4 based on the amount of winding-up of the wire 51 of the first pulling apparatus 5 and the amount of winding-up of the wire 61 of the second pulling apparatus 6 that have been calculated and the total lengths of the wires 51 and 61. The total lengths of the wires 51 and 61 are set, for example, in the memory 72 or the like in advance.

The control apparatus 7 calculates a distance R (hereinafter this distance will be referred to as a walking trainee distance R) between the position of the walking trainee (e.g., the center of the walking assistance apparatus 4) and the reference position $S_0$ of the treadmill 2 based on the length La of the wire 51 from the position of the first pulling apparatus 5 to the position of the walking assistance apparatus 4, the length Lb of the wire 61 from the position of the second pulling apparatus 6 to the position of the walking assistance apparatus 4, and a distance h from the upper side of the frame main body 3 to the walking assistance apparatus 4. The distance h from the upper side of the frame main body 3 to the walking assistance apparatus 4 is set, for example, in the memory 72 in advance.

When it is determined that the calculated walking trainee distance R has become equal to or larger than a predetermined distance Rs in the walking front/back direction while the walking trainee is walking on the treadmill 2, the control apparatus 7 controls the assisting power of the walking assistance apparatus 4 in such a way as to cause the walking trainee to approach the reference position $S_0$. The predetermined distance Rs is set, for example, in the memory 72 or the like in advance, and can be arbitrarily set by the walking trainee, the trainer and the like.

For example, when it is determined that the calculated walking trainee distance R has become equal to or larger than the predetermined distance Rs in the walking forward direction while the walking trainee is walking on the treadmill 2, the control apparatus 7 performs control to decrease the assisting power of the walking assistance apparatus 4 in such a way as to cause the walking trainee to approach the reference position $S_0$. Accordingly, it is possible to cause the walking trainee to move backward and approach the reference position $S_0$.

When it is determined that the calculated walking trainee distance R has become equal to or larger than the predetermined distance Rs in the walking backward direction while the walking trainee is walking on the treadmill 2, the control apparatus 7 performs control to increase the assisting power of the walking assistance apparatus 4 in such a way as to cause the walking trainee to approach the reference position $S_0$. Accordingly, it is possible to cause the walking trainee to move forward and approach the reference position $S_0$.

When it is determined that the calculated walking trainee distance R has become equal to or larger than the predetermined distance Rs in the walking forward direction, the control apparatus 7 may perform control to further decrease the assisting power of the walking assistance apparatus 4 in such a way as to cause the walking trainee to approach the reference position $S_0$ as the difference between the walking trainee distance R and the predetermined distance Rs becomes larger. In a similar way, when it is determined that the calculated walking trainee distance R has become equal to or larger than the predetermined distance Rs in the walking backward direction, the control apparatus 7 may perform control to further increase the assisting power of the walking assistance apparatus 4 in such a way as to cause the walking trainee to approach the reference position $S_0$ as the difference between the walking trainee distance R and the predetermined distance Rs becomes larger. Accordingly, even when the walking trainee is far away from the reference position $S_0$, the walking trainee is able to approach the reference position $S_0$ more rapidly.

A method of controlling the assisting power by the walking assistance apparatus 4 will be explained in detail. When the calculated walking trainee distance R is smaller than the predetermined distance Rs in the walking forward direction, the control apparatus 7 performs control, for example, in such a way that a normal assisting power f is generated in the walking assistance apparatus 4.

When it is determined that the calculated walking trainee distance R has become equal to or larger than the predetermined distance Rs in the walking forward direction, the control apparatus 7 performs control in such a way that the corrected assisting power F (F=f−Δf) obtained by subtracting a stride correction force Δf from the normal assisting power f is generated in the walking assistance apparatus 4 in such a way as to cause the walking trainee to approach the reference position $S_0$.

On the other hand, when it is determined that the calculated walking trainee distance R has become equal to or larger than the predetermined distance Rs in the walking backward direction, the control apparatus 7 performs control in such a way that the corrected assisting power F (F=f+Δf) obtained by adding the stride correction force Δf to the normal assisting power f is generated in the walking assistance apparatus 4 in such a way as to cause the walking trainee to approach the reference position $S_0$.

The aforementioned stride correction force Δf is calculated by the following expression.

Stride correction force Δf=G×|walking trainee distance R−predetermined distance Rs|

In the aforementioned expression, G denotes a gain, and is set, for example, in the memory 72 in advance.

The control apparatus 7 may calculate the stride correction force Δf using a function go as shown below.

Stride correction force Δf=g(|walking trainee distance R−predetermined distance Rs|)

The aforementioned function g( ) is, for example, a quadratic function or an exponential function.

The control apparatus 7 may calculate the stride correction force Δf based on map information indicating the relation between the stride correction force Δf and |walking trainee distance R−predetermined distance Rs|. The map information is experimentally obtained and set in the memory 72. The control apparatus 7 may automatically generate the map information based on data acquired during the walking training.

As described above, when at least one of the walking training amount of the walking trainee, the walking training level of the walking trainee set in the walking training system 1, and the speed of the treadmill 2 is larger/higher/greater than a predetermined amount, level and speed, the control apparatus 7 increases the predetermined distance Rs.

When the walking training amount of the walking trainee is larger than a predetermined amount, the control apparatus 7 increases the predetermined distance Rs set in the memory 72. When, for example, the walking training amount of the walking trainee is larger than a predetermined amount, the control apparatus 7 increases the predetermined distance Rs by multiplying the predetermined distance Rs set in the memory 62 by a predetermined coefficient. The predetermined coefficient is set in the memory 62 in advance and can be arbitrarily set by the walking trainee, the trainer and the like.

The walking training amount is, for example, the walking training time, the number of times that the walking trainee has performed the walking training, and the like using the walking training system 1. This walking training amount may be input to, for example, the control apparatus 7 via the display unit 8 or the like. Alternatively, the control apparatus 7 may automatically measure the walking training amount of the walking trainee (e.g., walking training time) and store the result of the measurement in the memory 72 or the like.

The aforementioned predetermined amount is experimentally set in a range that can prevent the walking trainee from falling from the treadmill 2 or colliding with the frame main body 3 by, for example, increasing or decreasing the speed of the treadmill 2 after detecting the deviation from the reference position $S_0$ on the basis of a person whose medical condition is severe or a person who has never performed walking training before. The predetermined amount is set, for example, in the memory 72 in advance, and can be arbitrarily set by the walking trainee, the trainer and the like.

When the walking training amount of the walking trainee is larger than the predetermined amount, the control apparatus 7 increases the predetermined distance Rs by multiplying, for example, the predetermined distance Rs set in the memory 72 by the predetermined coefficient. The predetermined coefficient is set in the memory 72 in advance and can be arbitrarily set by the walking trainee, the trainer and the like.

Figure 4:
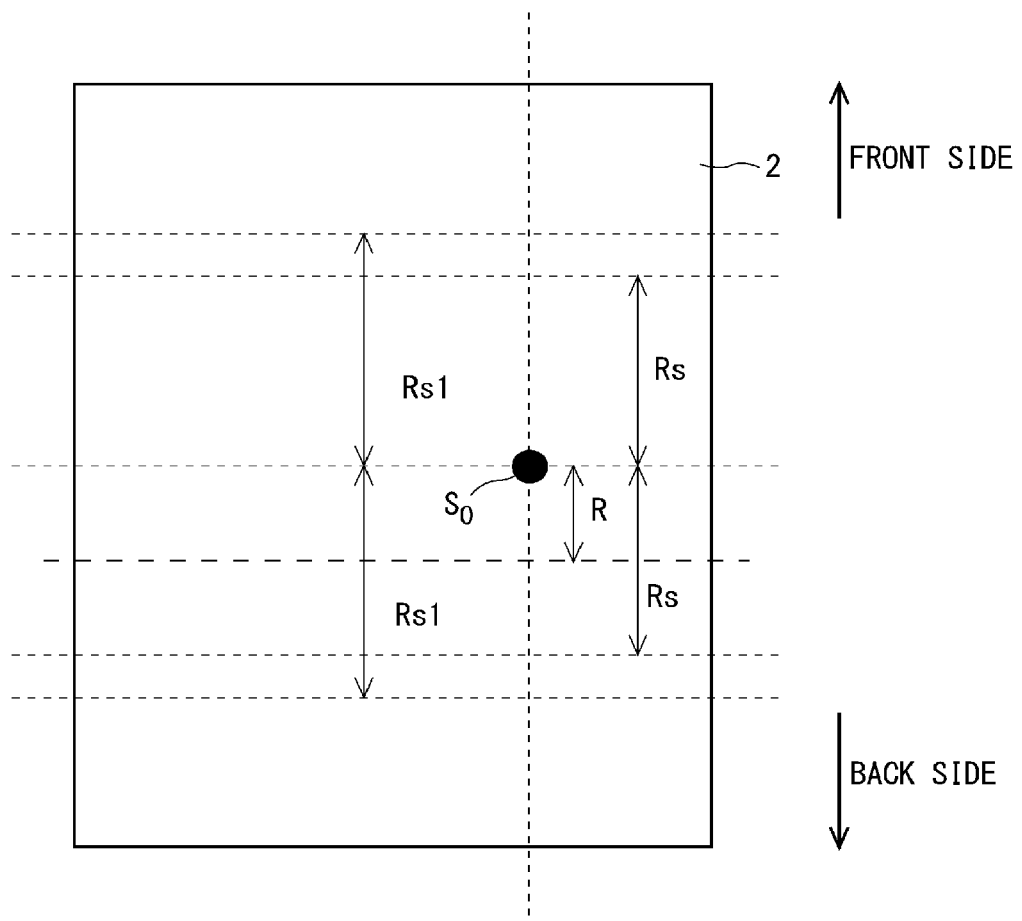
FIG. 4 is a diagram showing a predetermined distance when it is viewed from above.

FIG. 4 is a diagram showing the predetermined distance when it is viewed from above. When the walking training amount of the walking trainee is larger than the predetermined amount, the control apparatus 7 increases the predetermined distance Rs and changes the setting thereof to a predetermined distance Rs1 (Rs1>Rs).

When the walking training level of the walking trainee is higher than the predetermined level, the control apparatus 7 may increase the predetermined distance Rs set in the memory 72. The walking training level of the walking trainee indicates, for example, how well the walking trainee uses the walking training system 1, and is indicated by, for example, L1 to L10. The walking training level of the walking trainee is set, for example, in the memory 72 or the like in advance.

The control apparatus 7 may increase the predetermined distance Rs set in the memory 72 when the speed of the treadmill 2 is higher than the predetermined speed. The control apparatus 7 calculates the speed of the belt 21 of the treadmill 2 based on, for example, the value of the sensor 5 that detects the rotation of the motor of the treadmill 2.

Further, the control apparatus 7 may increase the predetermined distance Rs set in the memory 72 as the walking training amount of the walking trainee, the walking training level, or the speed of the treadmill 2 increases.

Figure 5:
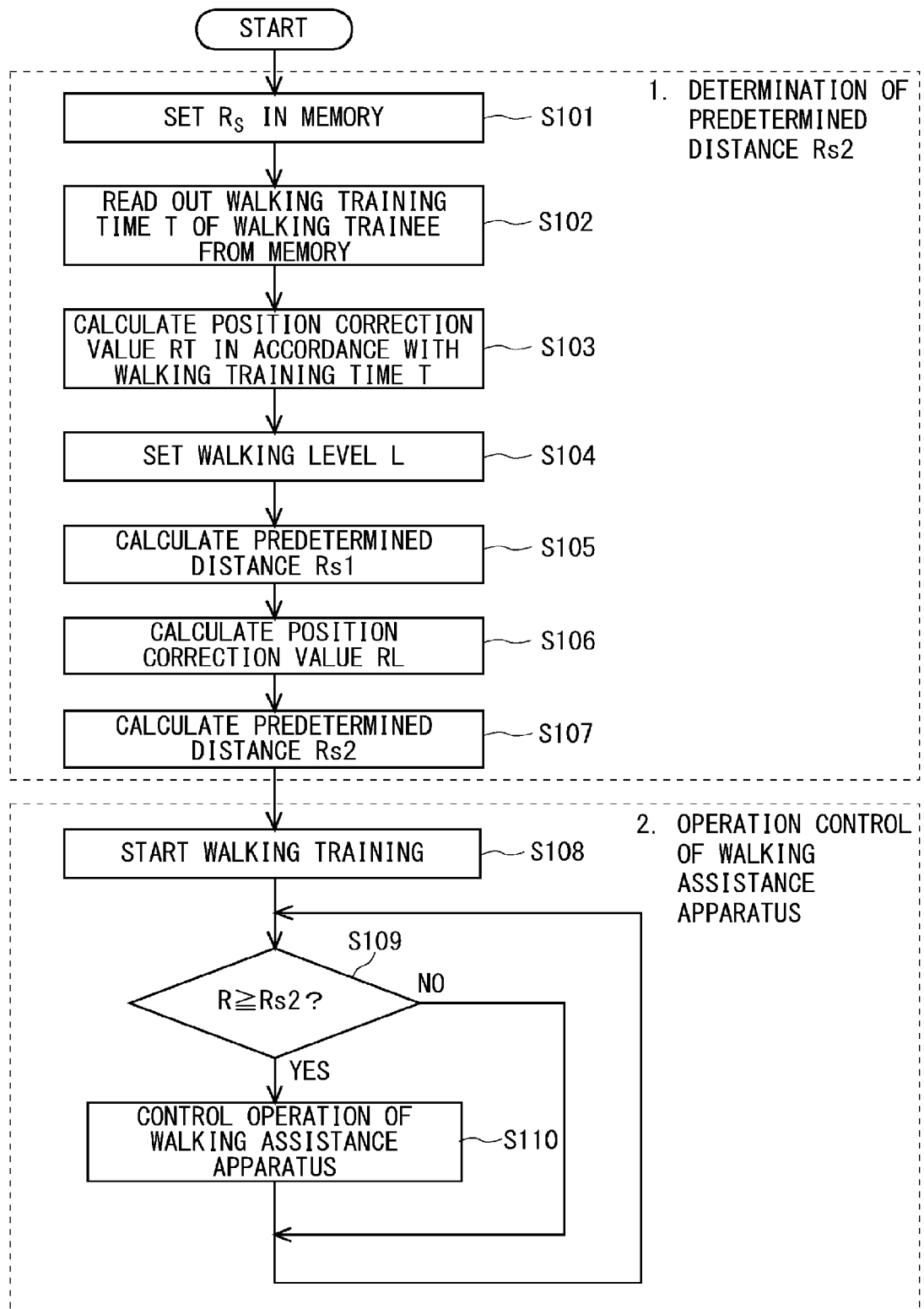
FIG. 5 is a flowchart showing a method of controlling the walking training system according to the first embodiment of the present disclosure.

FIG. 5 is a flowchart showing a method of controlling the walking training system according to the first embodiment.

The predetermined distance Rs is set in the memory 72 (Step S101).

The control apparatus 7 reads out a walking training time T of the walking trainee stored in the memory 72 (Step S102).

The control apparatus 7 calculates a position correction value RT by multiplying the walking training time T by a correction coefficient Rh (Step S103).

Position correction value $RT$=walking training time $T$×correction coefficient $Rh$ The correction coefficient Rh is set, for example, in the memory 72 or the like in advance.

A walking training level L of the walking trainee is set in the control apparatus 7 (Step S104).

The control apparatus 7 calculates the increased predetermined distance Rs1 by adding the calculated position correction value RT to the predetermined distance Rs (Step S105).

Predetermined distance $Rs1$=predetermined distance $Rs$+position correction value $RT$ The control apparatus 7 calculates a position correction value RL by multiplying the walking training level L by a correction coefficient R1 (Step S106).

Position correction value $RL$=walking training level $L$×correction coefficient $R1$ The correction coefficient R1 is set, for example, in the memory 72 or the like in advance.

The control apparatus 7 adds the aforementioned position correction value RL to the predetermined distance Rs1 calculated in the above (Step S104), thereby calculating an increased predetermined distance Rs2 (Step S107).

Predetermined distance $Rs2$=predetermined distance $Rs1$+position correction value $RL$ The control apparatus 7 drives the treadmill 2 and starts the walking training (Step S108). The control apparatus 7 determines whether the walking trainee distance R is equal to or larger than the predetermined distance Rs2 (Step S109).

When it is determined that the walking trainee distance R is equal to or larger than the predetermined distance Rs2 (YES in Step S109), the control apparatus 7 controls the operation of the walking assistance apparatus 4 in such a way as to cause the walking trainee to approach the reference position $S_0$ (Step S110). The control apparatus 7 may appropriately determine whether the walking trainee distance R is equal to or larger than the predetermined distance Rs1, thereby executing the control of the walking assistance apparatus 4.

As described above, the walking training system 1 according to the first embodiment controls, when the walking trainee is spaced apart from the reference position of the treadmill 2 by the predetermined distance or more in the walking front/back direction while the walking trainee is walking on the treadmill 2, the operation of the walking assistance apparatus 4 in such a way as to cause the walking trainee to approach the reference position, and increases the predetermined distance when at least one of the walking training amount of the walking trainee, the walking training level of the walking trainee set in the walking training system 1, and the speed of the treadmill 2 is larger/higher/greater than a predetermined amount, level and speed. Accordingly, it is possible to achieve both continuity of the walking training and suppression of the reduction in the training effect in accordance with the walking level of each walking trainee.

Second Embodiment

In a second embodiment of the present disclosure, the control apparatus 7 controls the operation of the walking assistance apparatus in such a way as to cause the walking trainee to approach the reference position $S_0$ when the calculated walking trainee distance R becomes equal to or larger than a first predetermined distance in the walking forward direction or when the calculated walking trainee distance R becomes equal to or larger than a second predetermined distance in the walking backward direction. The first predetermined distance on the front side of the walking training system is set to be larger than the second predetermined distance on the back side of the walking training system.

When, for example, the medical condition of the walking trainee is severe, the walking trainee is more likely to be forced to move backward than forward since the trainee cannot catch up with the speed of the treadmill 2. Therefore, the size of a dead area, which is an area where the adjustment control of the assisting power of the walking assistance apparatus 4 is not performed, in the front side of the walking training system is preferably set to be larger than that in the back side of the walking training system. That is, as described above, the first predetermined distance is set to be larger than the second predetermined distance. Accordingly, it is possible to set a more optimal dead area and to achieve both continuity of the walking training and suppression of the reduction in the training effect more optimally.

Figure 6:
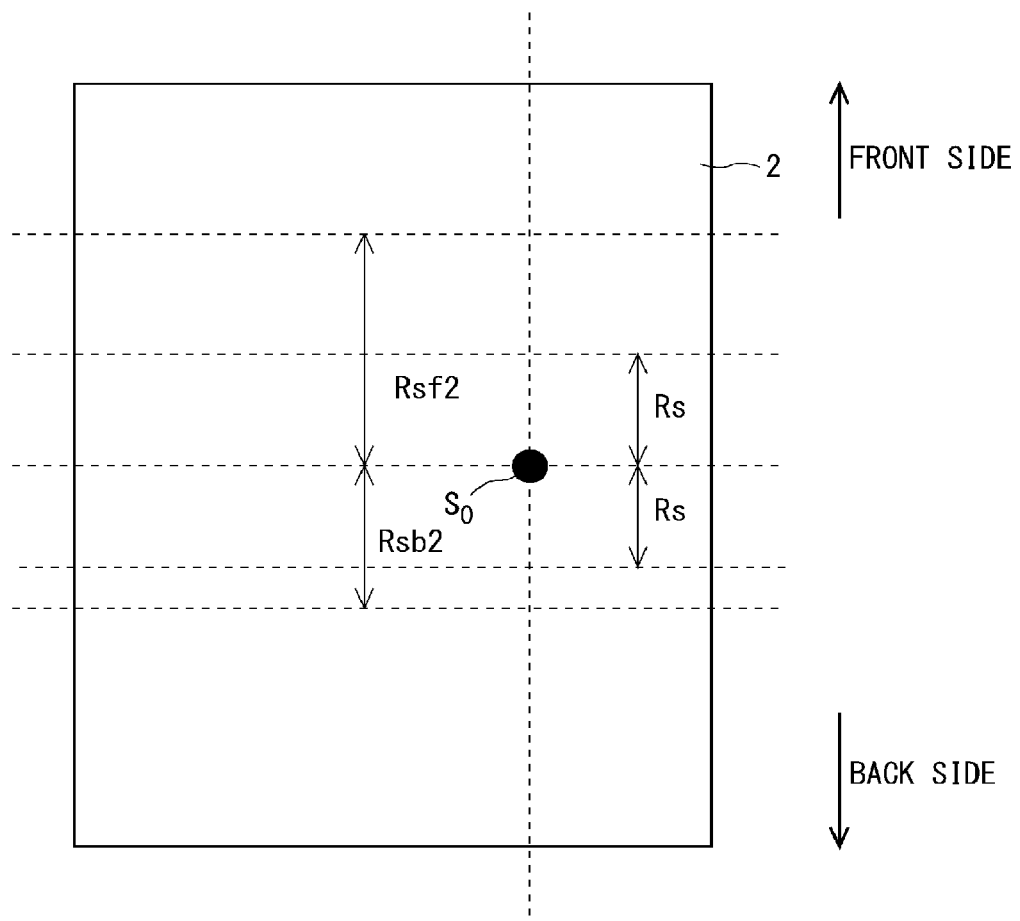
FIG. 6 is a diagram showing one example in which a first predetermined distance on a front side of the walking training system is set to be larger than a second predetermined distance on a back side of the walking training system.

Next, a method of controlling the walking training system according to the second embodiment will be explained in detail. FIG. 6 is a diagram showing one example in which the first predetermined distance on the front side of the walking training system is set to be larger than the second predetermined distance on the back side of the walking training system.

(When a walking trainee distance is equal to or larger than the first predetermined distance in the walking forward direction)

The control apparatus 7 calculates a position correction value RTf by multiplying the walking training time T by the correction coefficient Rh and a forward/backward correction coefficient kh.

Position correction value $RTf$=walking training time $T$×correction coefficient $Rh$×forward/backward correction coefficient $kh$ The forward/backward correction coefficient kh (kh>1) is set, for example, in the memory 72 in advance.

The control apparatus 7 calculates an increased predetermined distance Rsf1 by adding the calculated position correction value RTf to the predetermined distance Rs.

Predetermined distance $Rsf1$=predetermined distance $Rs$+position correction value $RTf$ The control apparatus 7 calculates the position correction value RLf by multiplying the walking training level L by the correction coefficient R1 and a forward/backward correction coefficient kl.

Position correction value $RLf$=walking training level $L$×correction coefficient $R1$×forward/backward correction coefficient $kl$ The forward/backward correction coefficient kl (kl>1) is set, for example, in the memory 72 in advance.

The control apparatus 7 adds the aforementioned position correction value RLf to the calculated predetermined distance Rsf1, thereby calculating an increased first predetermined distance Rsf2.

First predetermined distance $Rsf2$=predetermined distance $Rsf1$+position correction value $RLf$ When the calculated walking trainee distance R becomes equal to or larger than the first predetermined distance Rsf2 in the walking forward direction, the control apparatus 7 executes control to reduce the assisting power of the walking assistance apparatus 4 in such a way as to cause the walking trainee to approach the reference position $S_0$.

(When a walking trainee distance becomes equal to or larger than the second predetermined distance in the walking backward direction)

The control apparatus 7 calculates a position correction value RTb by multiplying the walking training time T by the correction coefficient Rh.

Position correction value $RTb$=walking training time $T$×correction coefficient $Rh$ The control apparatus 7 adds the calculated position correction value RTb to the predetermined distance Rs, thereby calculating an increased predetermined distance Rsb1.

Predetermined distance $Rsb1$=predetermined distance $Rs$+position correction value $RTb$ The control apparatus 7 calculates the position correction value RLb by multiplying the walking training level L by the correction coefficient R1.

Position correction value $RLb$=walking training level $L$×correction coefficient $R1$ The control apparatus 7 adds the aforementioned position correction value RLb to the calculated predetermined distance Rsb1, thereby calculating an increased second predetermined distance Rsb2.

Second predetermined distance $Rsb2$=predetermined distance $Rsb1$+position correction value $RLb$ When the calculated walking trainee distance R becomes equal to or larger than the second predetermined distance Rsb2 in the walking backward direction, the control apparatus 7 executes control to increase the assisting power of the walking assistance apparatus 4 in such a way as to cause the walking trainee to approach the reference position $S_0$.

Since the other configurations of the second embodiment are substantially the same as those of the aforementioned first embodiment, the same components are denoted by the same reference symbols and detailed descriptions thereof will be omitted.

Third Embodiment

In a third embodiment of the present disclosure, when the walking trainee is spaced apart from the reference position $S_0$ of the treadmill 2 by the predetermined distance Rs or more in the walking front/back direction while the walking trainee is walking on the treadmill 2, the control apparatus 7 may perform, besides control of the operation of the walking assistance apparatus 4, at least control of either the pulling forces of the first and second pulling apparatuses 5 and 6, or the speed and the inclination of the treadmill 2 in such a way as to cause the walking trainee to approach the reference position $S_0$.

Accordingly, when the walking trainee is spaced apart from the reference position of the treadmill 2 by the predetermined distance or more in the walking front/back direction, it is possible to cause the walking trainee to approach the reference position $S_0$ more rapidly using not only the operation of the walking assistance apparatus 4 but also the pulling forces of the first and second pulling apparatuses 5 and 6, and the speed and/or the inclination of the treadmill 2.

For example, when it is determined that the calculated walking trainee distance R has become equal to or larger than the predetermined distance Rs in the walking forward direction, the control apparatus 7 may perform, besides the control to decrease the assisting power of the walking assistance apparatus 4, at least one of control to cause the belt 21 of the treadmill 2 to be in the upward inclined state and control to increase the speed of the belt 21 of the treadmill 2. Accordingly, it is possible to cause the walking trainee to move backward more rapidly so that the walking trainee can approach the reference position $S_0$ by using not only the assisting power of the walking assistance apparatus 4 but also the increase in the speed of the treadmill 2 or the upward inclination thereof.

On the other hand, when it is determined that the calculated walking trainee distance R has become equal to or larger than the predetermined distance Rs in the walking backward direction, the control apparatus 7 may perform, besides the control to increase the assisting power of the walking assistance apparatus 4, at least one of control to cause the belt 21 of the treadmill 2 to be in the downward inclined state and control to decrease the speed of the belt 21 of the treadmill 2. Accordingly, it is possible to cause the walking trainee to move forward more rapidly so that the walking trainee can approach the reference position $S_0$ by using not only the assisting power of the walking assistance apparatus 4 but also the decrease in the speed of the treadmill 2 or the downward inclination thereof.

Further, when, for example, it is determined that the calculated walking trainee distance R has become equal to or larger than the predetermined distance Rs in the walking forward direction, the control apparatus 7 may perform, besides the control to increase the assisting power of the walking assistance apparatus 4, control to increase backward horizontal components of the pulling forces of the first and second pulling apparatuses 5 and 6. Accordingly, it is possible to cause the walking trainee to move backward more rapidly so that the walking trainee can approach the reference position $S_0$ by using not only the assisting power of the walking assistance apparatus 4 but also the pulling forces of the first and second pulling apparatuses 5 and 6.

On the other hand, when it is determined that the calculated walking trainee distance R has become equal to or larger than the predetermined distance Rs in the walking backward direction, the control apparatus 7 may perform, along with the control to increase the assisting power of the walking assistance apparatus 4, control to increase forward horizontal components of the pulling forces of the first and second pulling apparatuses 5 and 6. Accordingly, it is possible to cause the walking trainee to move forward more rapidly so that the walking trainee can approach the reference position $S_0$ by using not only the assisting power of the walking assistance apparatus 4 but also the pulling forces of the first and second pulling apparatuses 5 and 6.

Since the other structures of the third embodiment are substantially the same as those of the first embodiment, the same components are denoted by the same reference symbols and detailed descriptions thereof will be omitted.

The present disclosure is not limited to the aforementioned embodiments and may be changed as appropriate without departing from the spirit of the present disclosure.

In the aforementioned embodiments, the control apparatus 7 controls the speed of the treadmill 2 in such a way as to cause the walking trainee to approach the reference position $S_0$ by comparing the walking trainee distance R with the predetermined distance Rs. However, this configuration is merely one example. The control apparatus 7 may control the assisting power of the walking assistance apparatus 4 in such a way as to cause the walking trainee to approach the reference position $S_0$ by comparing a ratio Lpf of the length of the wire 51 of the first pulling apparatus 5 to the length of the wire 61 of the second pulling apparatus 6 when the walking assistance apparatus 4 is located at the position of the predetermined distance Rs spaced apart from the reference position $S_0$ in the forward walking direction, a ratio Lpb of the length of the wire 51 of the first pulling apparatus 5 to the length of the wire 61 of the second pulling apparatus 6 when the walking assistance apparatus 4 is located at the position of the predetermined distance Rs spaced apart from the reference position $S_0$ in the backward walking direction, and a ratio Lp (e.g., Lp=Lb/La) of the current length of the wire 51 of the first pulling apparatus 5 to the current length of the wire 61 of the second pulling apparatus 6.

When it is determined that the ratio Lp of the current length of the wire 51 of the first pulling apparatus 5 to the current length of the wire 61 of the second pulling apparatus 6 is larger than the ratio Lpf of the length of the wire 51 of the first pulling apparatus 5 to the length of the wire 61 of the second pulling apparatus 6 when the walking assistance apparatus 4 is located at the position of the predetermined distance Rs spaced apart from the reference position $S_0$ in the forward walking direction (Lp>Lpf), the control apparatus 7 performs control to decrease the assisting power of the walking assistance apparatus 4. On the other hand, when it is determined that the ratio Lp of the current length of the wire 51 of the first pulling apparatus 5 to the current length of the wire 61 of the second pulling apparatus 6 is smaller than the ratio Lpb of the length of the wire 51 of the first pulling apparatus 5 to the length of the wire 61 of the second pulling apparatus 6 when the walking assistance apparatus 4 is located at the position of the predetermined distance Rs spaced apart from the reference position $S_0$ in the backward walking direction (Lp<Lpb), the control apparatus 7 performs control to increase the assisting power of the walking assistance apparatus 4.

In the aforementioned embodiments, the control apparatus 7 calculates the walking trainee distance R based on the amount of winding-up of each of the wires 51 and 61 of the first and second pulling apparatuses 5 and 6, respectively. However, this configuration is merely one example.

For example, the control apparatus 7 may calculate the distance R based on a load value of a load sensor provided in the treadmill 2. The treadmill 2 is provided with a plurality of load sensors. The control apparatus 7 calculates the location of the walking trainee on the treadmill 2 based on the load value detected by each of the load sensors. The control apparatus 7 calculates the walking trainee distance R based on the calculated location of the walking trainee and the reference position $S_0$ of the treadmill 2.

The control apparatus 7 may calculate the predetermined distance Rs based on images of the walking trainee walking on the treadmill 2 captured by a camera. The control apparatus 7 performs image processing on the images of the walking trainee walking on the treadmill 2 captured by the camera to specify the location of the walking trainee and the reference position $S_0$ of the treadmill 2, thereby calculating the walking trainee distance R between them.

In the aforementioned embodiments, the first and second pulling apparatuses 5 and 6 are configured to pull the walking assistance apparatus 4 of the walking trainee upwardly. However, this structure is merely one example. A structure in which the single pulling apparatus 5 is provided near the intermediate part in the upper part of the frame main body 3 and the pulling apparatus 5 pulls the attachment of the walking trainee upwardly may instead be employed. Further, the first and second pulling apparatuses 5 and 6 may not be provided in the frame main body 3.

The structures of the aforementioned embodiments may be combined with one another as appropriate.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A walking training system comprising:
   a treadmill on which a walking trainee walks;
   a walking assistance apparatus that is mounted on a leg part of the walking trainee and assists walking of the walking trainee; and
   a controller for controlling an operation of the walking assistance apparatus,
   wherein
   the controller controls the operation of the walking assistance apparatus in such a way as to cause the walking trainee to approach a reference position when the walking trainee is spaced apart from the reference position of the treadmill by a predetermined distance or more in a walking front or back direction while the walking trainee is walking on the treadmill, and
   the controller increases the predetermined distance when at least one of a walking training amount of the walking trainee is larger than a predetermined amount, a walking training level of the walking trainee set in the walking training system is higher than a predetermined level, and a speed of the treadmill is greater than a predetermined speed.

2. The walking training system according to claim 1, wherein
   the controller performs control to decrease an assisting power of the walking assistance apparatus in such a way as to cause the walking trainee to approach the reference position when the walking trainee is spaced apart from the reference position of the treadmill by the predetermined distance or more in the walking front direction, and
   the controller performs control to increase the assisting power of the walking assistance apparatus in such a way as to cause the walking trainee to approach the reference position when the walking trainee is spaced apart from the reference position of the treadmill by the predetermined distance or more in the walking back direction.

3. The walking training system according to claim 1, wherein, when the walking trainee is spaced apart from the reference position of the treadmill by the predetermined distance or more in the walking front or back direction, the controller performs control to further increase or decrease an assisting power of the walking assistance apparatus in such a way as to cause the walking trainee to approach the reference position as the distance to the walking trainee from the reference position of the treadmill becomes greater in the walking front or back direction.

4. The walking training system according to claim 1, wherein
the controller controls the operation of the walking assistance apparatus in such a way as to cause the walking trainee to approach the reference position when the walking trainee is spaced apart from the reference position of the treadmill by the first predetermined distance or more in the walking front direction or when the walking trainee is spaced apart from the reference position of the treadmill by a second predetermined distance or more in the walking back direction, and
the first predetermined distance is set to be greater than the second predetermined distance.

5. The walking training system according to claim 1, wherein the controller controls, when the walking trainee is spaced apart from the reference position of the treadmill by the predetermined distance or more in the walking front or back direction, the operation of the walking assistance apparatus and at least one of the inclination and the speed of the treadmill and a pulling force of a pulling mechanism that pulls the walking trainee upward via a wire in such a way as to cause the walking trainee to approach the reference position.

6. A method of controlling a walking training system comprising:
a treadmill on which a walking trainee walks;
a walking assistance apparatus that is mounted on a leg part of the walking trainee and assists walking of the walking trainee; and
a controller for controlling an operation of the walking assistance apparatus,
wherein
the controller controls the operation of the walking assistance apparatus in such a way as to cause the walking trainee to approach a reference position when the walking trainee is spaced apart from the reference position of the treadmill by a predetermined distance or more in a walking front or back direction while the walking trainee is walking on the treadmill, and
the controller increases the predetermined distance when at least one of a walking training amount of the walking trainee is larger than a predetermined amount, a walking training level of the walking trainee set in the walking training system is higher than a predetermined level, and a speed of the treadmill is greater than a predetermined speed.

* * * * *